United States Patent
Chu

(10) Patent No.: US 7,293,803 B2
(45) Date of Patent: Nov. 13, 2007

(54) METHOD FOR INDICATING THE USER'S NAME ON A BLOOD-SAMPLING NEEDLE PEN AND THE PRODUCT THEREOF

(76) Inventor: Ching-Nan Chu, San Lung St., Shu Lin City, Taipei Hsien (TW)

( * ) Notice: Subject to any disclaimer, the term of this patent is extended or adjusted under 35 U.S.C. 154(b) by 496 days.

(21) Appl. No.: 10/735,873

(22) Filed: Dec. 16, 2003

(65) Prior Publication Data

US 2005/0131315 A1     Jun. 16, 2005

(51) Int. Cl.
*B42D 15/00* (2006.01)
(52) U.S. Cl. .................... 283/81; 600/583; 604/189
(58) Field of Classification Search ................. 283/81; 604/125, 189; 600/583, 584
See application file for complete search history.

(56) References Cited

U.S. PATENT DOCUMENTS

| | | | | |
|---|---|---|---|---|
| 3,703,174 A | * | 11/1972 | Smith | 604/159 |
| 3,885,562 A | * | 5/1975 | Lampkin | 604/189 |
| 3,965,898 A | * | 6/1976 | Cloyd | 604/203 |
| 4,300,678 A | * | 11/1981 | Gyure et al. | 206/364 |
| 4,921,277 A | * | 5/1990 | McDonough | 283/81 |
| 5,295,976 A | * | 3/1994 | Harris | 604/211 |
| 5,312,365 A | * | 5/1994 | Firth et al. | 604/189 |
| 5,692,640 A | * | 12/1997 | Caulfield et al. | 221/70 |
| 5,728,074 A | * | 3/1998 | Castellano et al. | 604/207 |
| 6,730,046 B1 | * | 5/2004 | Hamamoto et al. | 600/583 |
| 6,764,469 B2 | * | 7/2004 | Broselow | 604/207 |
| 6,966,897 B2 | * | 11/2005 | Shimazaki | 604/189 |
| 2004/0127818 A1 | * | 7/2004 | Roe et al. | 600/583 |
| 2004/0186437 A1 | * | 9/2004 | Frenette et al. | 604/189 |

* cited by examiner

*Primary Examiner*—Daniel W. Howell
(74) *Attorney, Agent, or Firm*—Leong C. Lei

(57) ABSTRACT

A method for indicating the user's name on a blood-sampling needle pen and the product thereof includes providing a see-through window on the housing of the blood-sampling needle pen, or having the housing made of transparent materials, forming a media compartment of hollow chamber inside of the housing such that a curled note indicating the user's name, the date and the relevant data, etc. can be inserted thereinto, covering a cap on the rear end of the blood-sampling needle pen, and mounting a dust cover on the front end of the blood-sampling needle pen, thereby forming a blood-sampling needle pen different from the disposable ones of the prior art for the purposes of enhancing economic and environmental effect.

3 Claims, 7 Drawing Sheets

METHOD FOR INDICATING THE USER'S NAME ON A BLOOD-SAMPLING NEEDLE PEN AND THE PRODUCT THEREOF

BACKGROUND OF THE INVENTION (a) Technical Field of the Invention

The present invention relates to a method for indicating the user's name on a blood-sampling needle pen and the product thereof, particularly to a blood-sampling needle pen having the design of a transparent housing which is provided with a media compartment for inserting a curled note indicating the user's name, the dates of first and continuous use and the relevant data, etc. The invention may allow the user to fill in his/her personal information and the relevant data of the blood-sampling, especially those diabetics and gout patients, they can do self blood-sampling at home periodically with the blood-sampling needle pen according to the invention, so as to avoid confusion with the other users.

(b) Description of the Prior Art

Generally, blood-sampling needles for medical use primarily include a needle holder and a needle provided at the center thereof. The needle holder utilized now a day is usually made of plastic material, and is combined with an extruding needle tip at one end. Those of the prior art used to be disposable after use without reuse. Under the circumstance, those used blood-sampling needles would become medical waste not being able to be collected and processed with general waste. Instead, they need be specially processed in a designated incinerator for those medical wastes. As such, considerable costs incurred for environmental process and the subsequent process would become a great burden.

In view of the above, a new product relating to a blood-sampling needle pen, which can be reused, has been disclosed, such as R.O.C. Patent Appln. No. 89103111 titled "Less Pain Blood-sampling Device", Appln. No. 89103112 titled "A Blood-sampling Device Able to Release a Connector" and Appln. No. 91212018 titled "Blood Sampler". The patents disclosed in the aforementioned applications relate to blood-sampling devices containing an invisible needle. Those blood-sampling devices are generally in the form of a pen to ease the user to hold by hand. Besides, the needle can shrink into the blood-sampling device after use, be repeatedly used and be kept and carried without any risk of pricking. Besides, as said blood sampling needles can be reused personally, it is quite efficient in environmental protection.

Notwithstanding this, if the user is a diabetic, he/she might have gotten such a hereditary disease from his/her family who could be diabetics as well. Therefore, some members of the family might need to do regular blood sampling at the same period of time. To avoid confusion, the best way is to clearly indicate the user's name on the personal blood sampling needle pen. Furthermore, medical institutions such as hospitals, homes for the aged, and medical care centers, etc. having a great number of patients need to specifically indicate the user's name on the blood sampling needle pen, in order to avoid confusion and inter-affection.

However, the blood sampling needle pens currently sold in the markets would not have the function of indicating the user's name thereon, rendering confusingly use with the others and make the users exposed to the risk of inter-affection. There exists a need of overcoming the issue.

Accordingly, the motive of disclosing the invention is to improve the afore-mentioned disadvantages in the prior art and to provide a method for easily indicating the user's name on the blood sampling needle pen and the product thereof.

SUMMARY OF THE INVENTION

The primary object of the invention is to provide a method for indicating the user's name on a blood sampling needle pen and the product thereof, which can permit easy indication of the user's name on the blood sampling needle pen without the risk of confusion and inter-affection.

The secondary object of the invention is to provide a method for indicating the user's name on the blood sampling needle pen and the product thereof, wherein a dust cover can be mounted on the top of the blood sampling needle pen for the purposes of keeping the product from dust during the period of non-use.

To obtain the above objects, the invention includes providing a see-through window on the housing of the blood-sampling needle pen, or having the housing made of transparent materials, forming a media compartment of hollow chamber inside of the housing such that a curled note indicating the user's name, the date and the relevant data, etc. can be inserted thereinto, and covering a cap on the rear end of the blood-sampling needle pen, thereby forming a blood-sampling needle pen for personal use without the confusion with the others, as well as forming a blood-sampling needle pen different from the disposable ones of the prior art for the purposes of enhancing economic and environmental effect. Furthermore, a dust cover can be mounted on the top of the blood-sampling needle pen for the purposes of keeping the product from dust during the period of non-use.

To completely appreciate these and other objects of the present invention as well as the invention itself, all of which will become apparent to those skilled in the art the following detailed description of the invention and the claims should be read in conjunction with the accompanying drawings.

DETAILED DESCRIPTION OF THE PREFERRED EMBODIMENT

Figure 1:
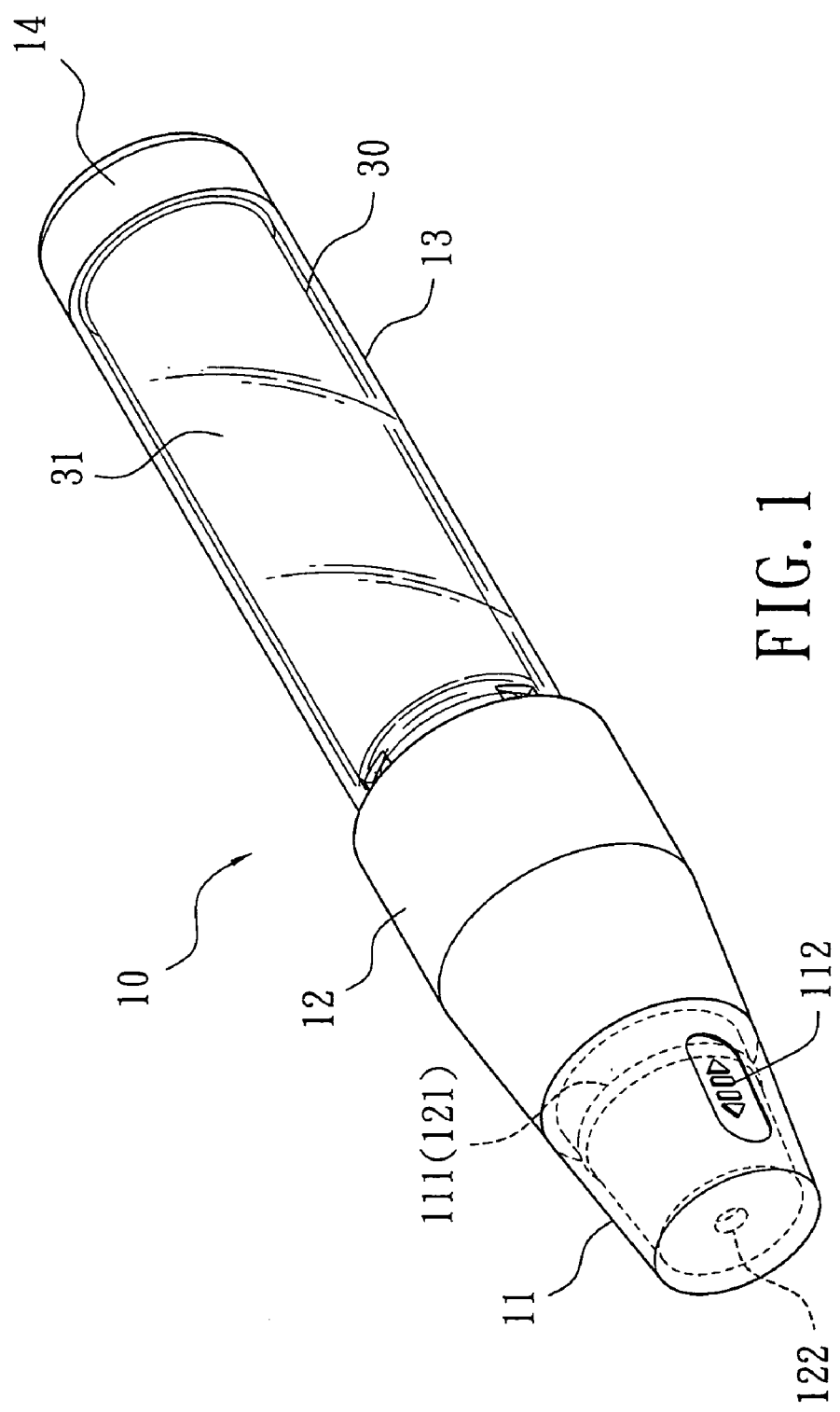
FIG. 1 is a perspective view of the present invention.
Figure 2:
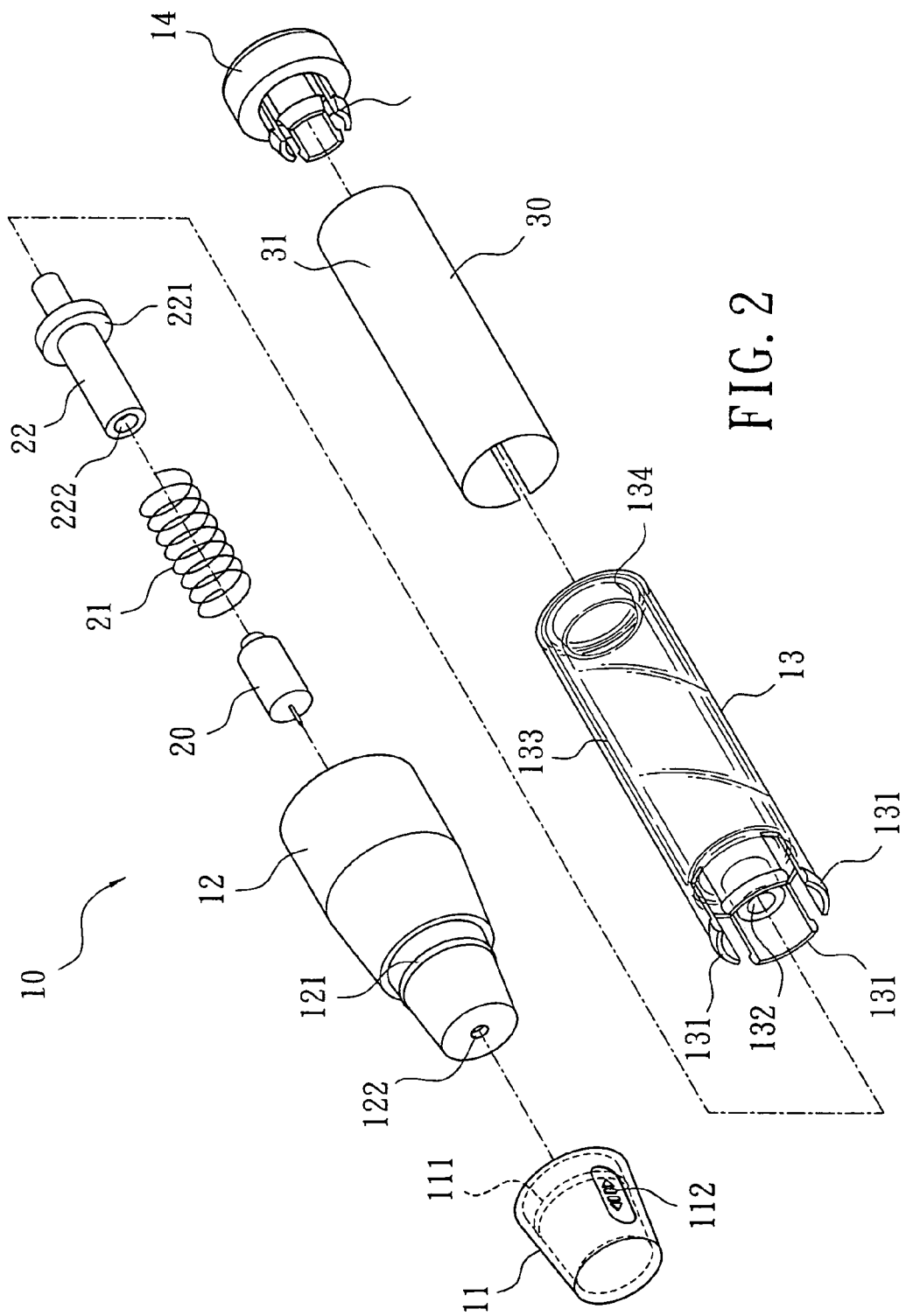
FIG. 2 is an exploded view of the present invention.

Referring to FIGS. 1 and 2, the present invention discloses a method for indicating the user's name on a blood-sampling needle pen and the product thereof, which is basically composed of a blood-sampling needle pen 10 and a note 30.

The blood-sampling needle pen 10 has a housing, which may include a dust cover 11, a front cap 12, a transparent body 13 and a rear cap 14. Besides, the invention further includes a needle 20, a spring 21, a needle holder 22 engaged in the housing, and a curled indication note 30 inserted into the transparent body 13, which can be easily visible from outside.

Figure 3:
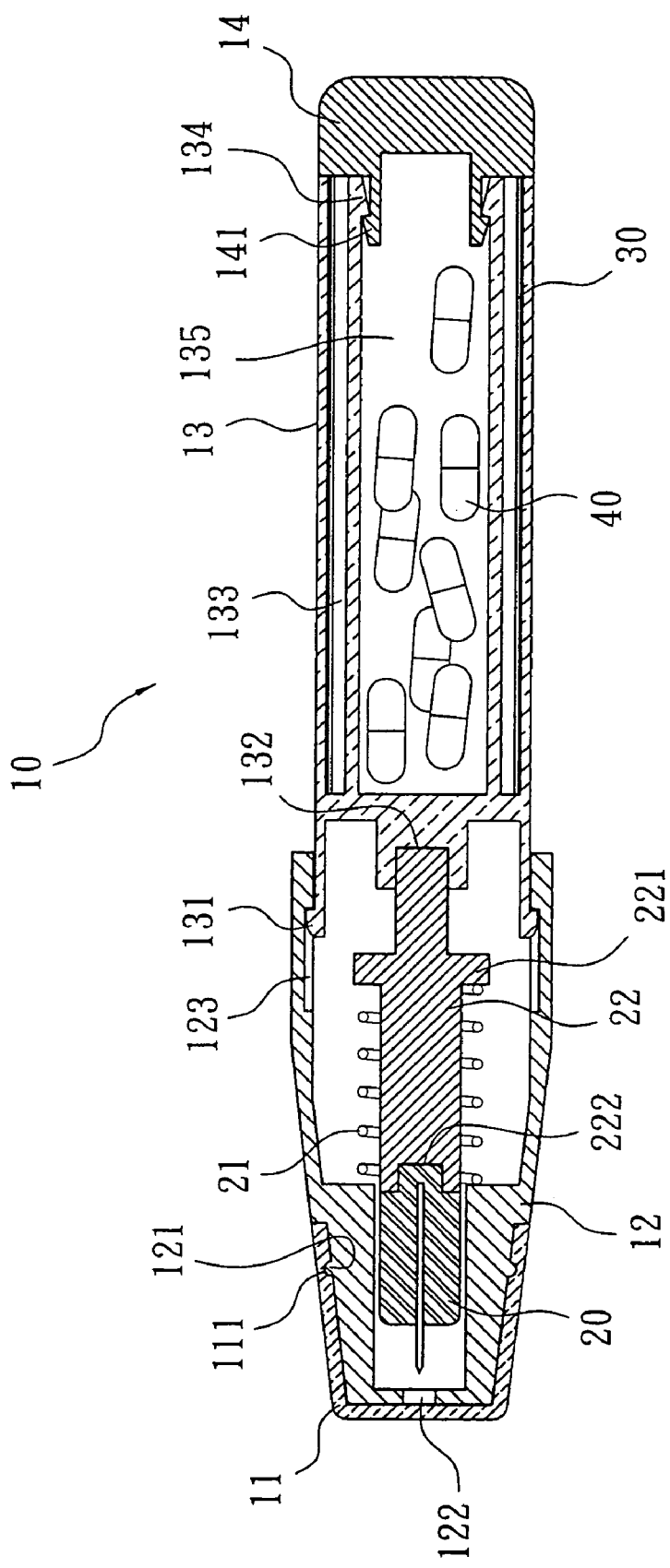
FIG. 3 is a perspective view of the invention after being assembled.

Referring to FIGS. 2 and 3, in the integral structure of the blood-sampling needle pen 10, a groove 111 is provided at the inner wall of the dust cover 11 for locking to a circle flange 121 provided at the front end of the front cap 12. Rugged lines 112 and hollow portions are provided at the sides of the exterior of the dust cover 11 the dust cover 12 to ease the user to hold and pull out by hand.

A through hole 122 is provided at the front center of the front cap 12 such that the needle can extrude therefrom for the purposes of blood-sampling, while a long groove 123 is provided in the inner wall of the rear end of the front cap 12 (as shown in FIG. 3).

The transparent body 13 is provided with a plurality of flexible lacking flakes 131 at the front end, a fish eye hole 132 at the center of the front edge, a housing with an interior circular compartment 133 made of transparent materials for receiving a note 30 indicated with the, user's name, and a bevel locking rim 134 at the rear end. The indicating note 30 can be visible from outside of the housing which is made of transparent materials, while the media compartment can be substituted by a hollow portion for the purposes distinction. Besides, the invention may have alternative embodiments, for example, having the housing provided with a hollow out frame (not shown) such that the indicating note can be visible from outside.

The rear cap 14, for mounting on the rear end of the housing 13, has a close end and a plurality of flexible locking flakes 141, which can slide along the bevel rear end of the housing and lock onto the locking rim 134.

When assembling the invention, the user must insert the rear end of the needle holder 22 into the fish eye hole 132 on the center of the transparent body to be against the spring by way of the locking rim 221 having a greater diameter. And then, the replaceable needle 20 is engaged in the hole 222 at the front end of the needle holder 22 such that the plurality of flexible locking flakes 131 can be locked and positioned in the long groove 123 at the inner wall of the front cap 12, thereby completing the assembly of the invention.

Figure 6:
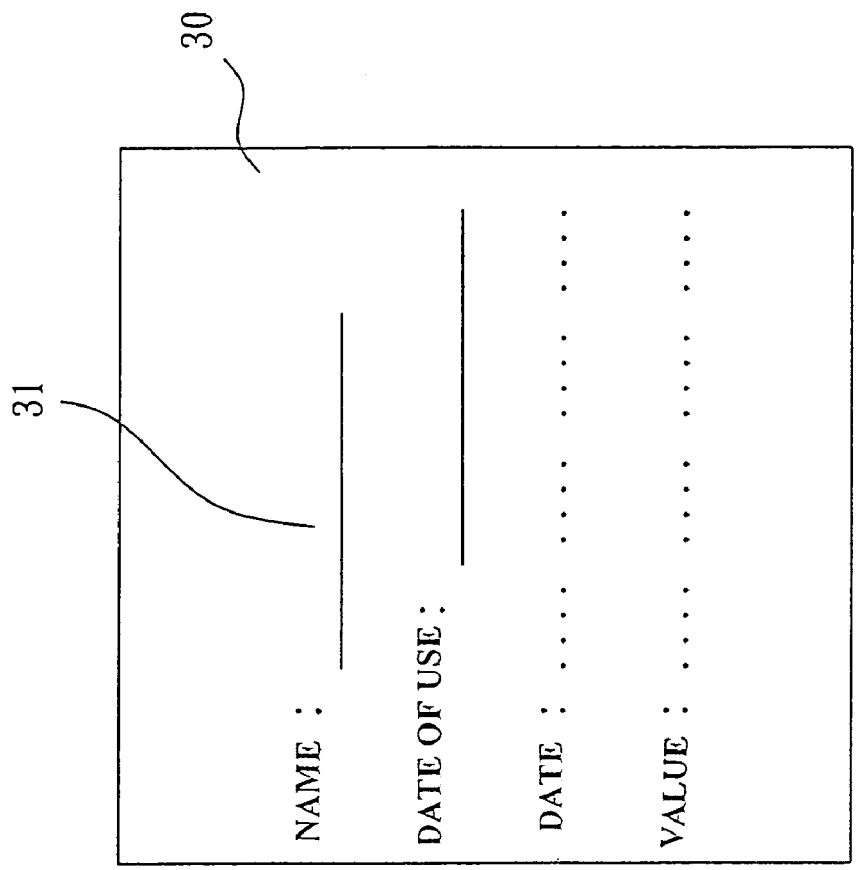
FIG. 6 shows the note applied to the invention.

The user can write down his/her name 31 and the relevant date of use and date (see FIG. 6), and curl and insert the indicating note 30 into the media compartment 133 provided in the transparent body 12 for easy distinction of the user.

Figure 4:
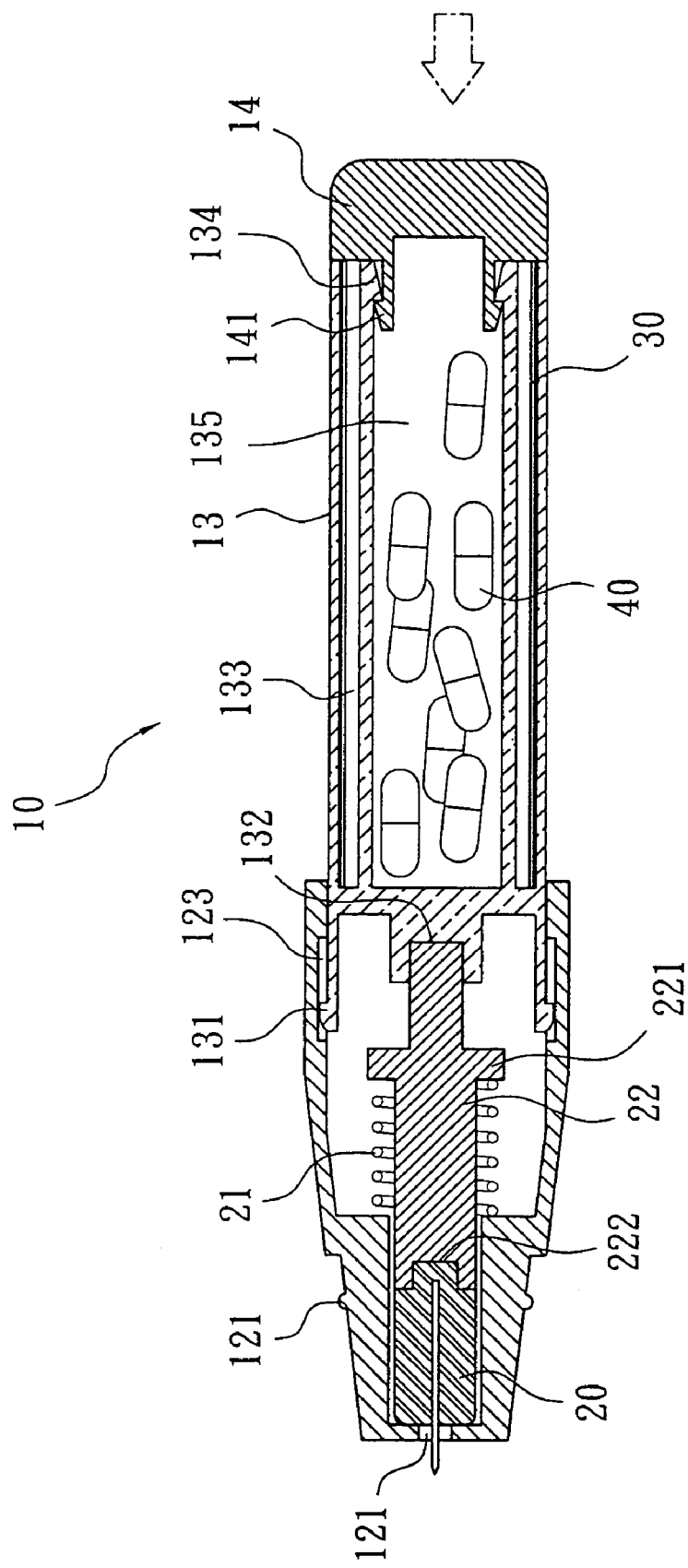
FIG. 4 is a perspective view of the invention in use status.

Referring to FIG. 4, when proceeding with the blood-sampling, the user must remove the dust cap 11 firstly, place the front cap on the finger tip (or any other portion on the skin appropriate for blood-sampling), push down the transparent body 13 to make the flexible locking flakes 131 move along the long groove 123 and transmit pressure through the needle holder 22 to the needle 20, thereby the needle will prick on the skin of the user for blood-sampling. After the needle is pulled out of the skin, it will return to the front cap 12 due to the elasticity of the spring 21 to prevent pricking the others.

It is worth a mention that the transparent body 13 of the blood-sampling needle pen 10 according to the invention is provided with a hollow portion 135 at the center for carrying medicines 40 to allow the user to take the medicine any time. Therefore, how close is the flexible locking flakes 141 on the rear cap 14 and the locking rim 123 at the rear end of the transparent body 13 depends on the need of the user who might need to remove the rear cap 14 for taking medicines outside of the hollow portion 135.

Figure 5:
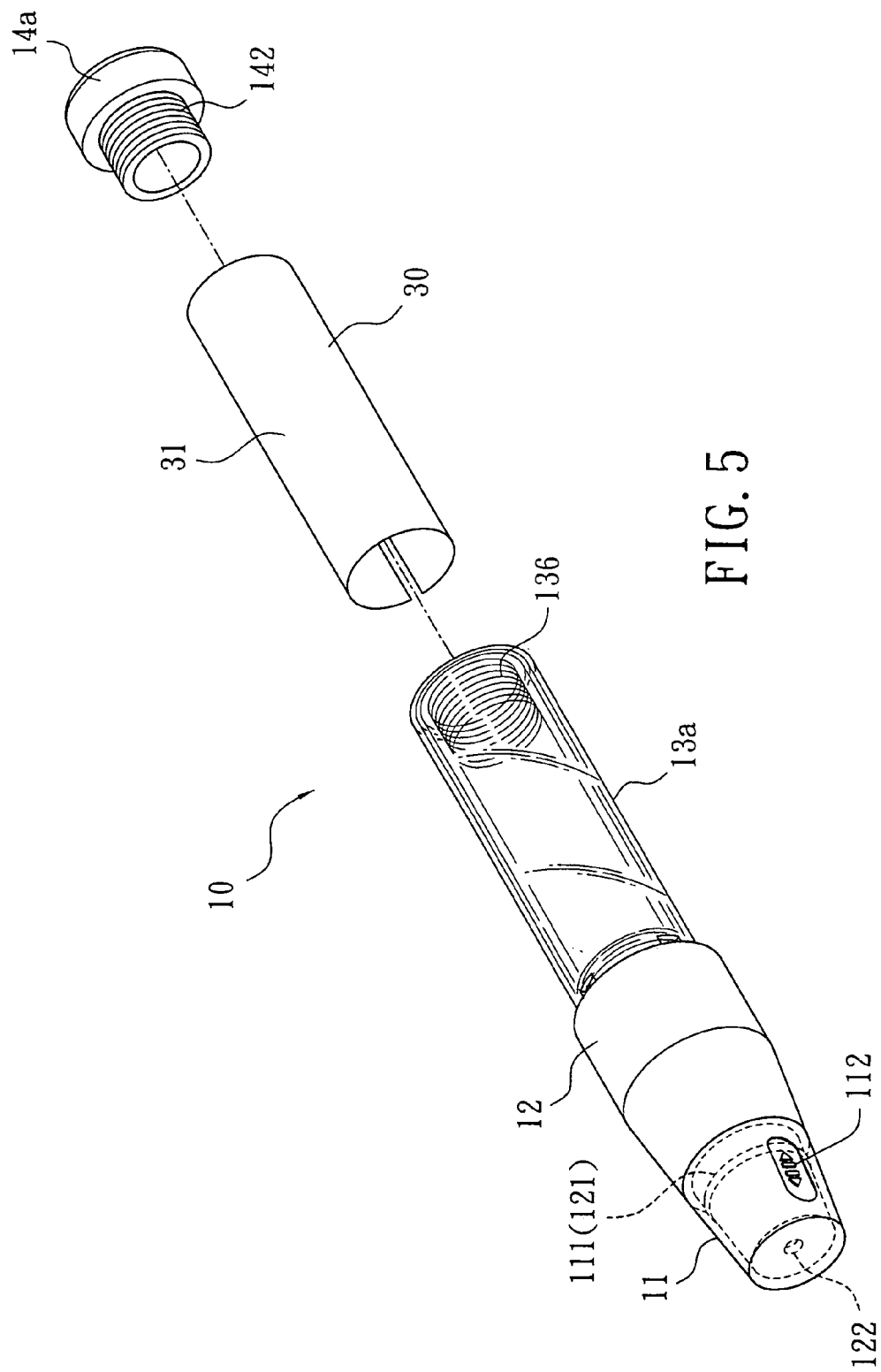
FIG. 5 is an exploded view of the invention.

Referring to FIG. 5, based on the afore-said technology theory, the rear cap 14a can be alternatively provided with exterior threads 142, and the transparent body 13a can be provided with interior threads 136 at the rear end, while a note 30 indicated with the user's name can be curled and inserted into the media compartment in the transparent body for clearly distinction.

Figure 7:
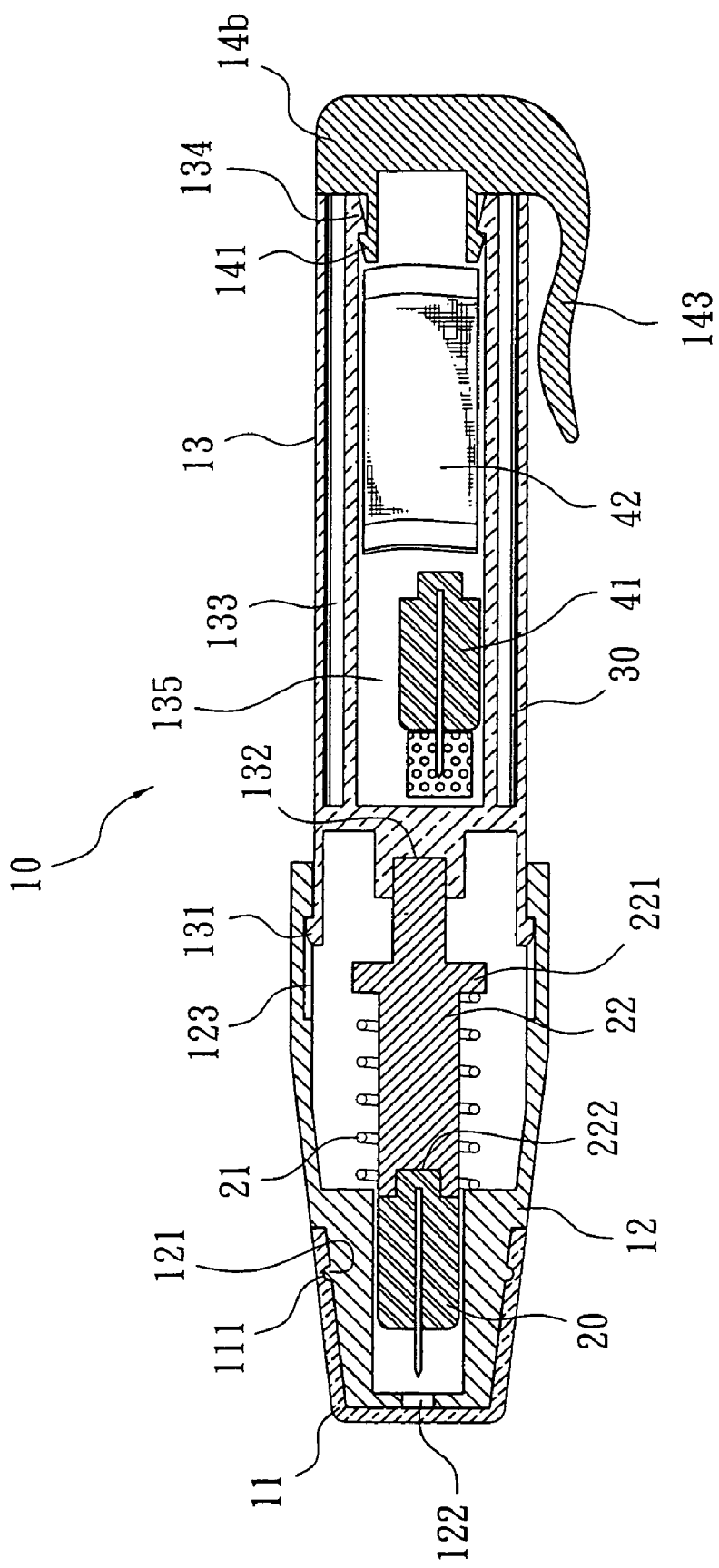
FIG. 7 is an exploded view of another embodiment according to the invention.

Referring to FIG. 7, in another embodiment of the invention, a pen clip 143 can be provided on the rear cap 14a to enable the user to carry the blood-sampling needle pen on his/her pocket or handbag outdoor. Besides, the hollow portion 135 in the center of the transparent body 13 can contain a supplemental needle 41 and/or wiping cotton 42 such that the user may replace the blood-sampling needle when necessary or clean the needle with the wiping cotton after use.

Concluded above, the purposes of the invention are to solve the issue of the prior art in which the blood-sampling needle cannot have a clear indication of the user's name or the relevant test data, and to provide a blood-sampling needle pen, which has better safety in use. Besides, while general blood-sampling needles of the prior art are made of non-transparent materials, it they are altered to be transparent or provided with a see-through window, the alteration should be restricted in view of the present invention. Given the blood-sampling needle is used by fixed person, it can be used repeatedly without the risk of inter-affection. Accordingly, the costs for a user who must use the blood-sampling needle would significantly reduced. In other words, the issue of processing the medical waste would relatively improved. The contribution to the environmental protection is remarkable. The invention is novel and rich of commercial value as claimed by the inventor.

I claim:

1. A method of indicating a user's name on a blood-sampling needle pen comprising steps of:
    (a) providing a see-through window on a housing of said blood-sampling needle;
    (b) forming a circular compartment in an interior of said housing, said housing having a first end and a second end;
    (c) inserting a curled note indicating a user's name, date and relevant data into said circular compartment;
    (d) providing a rear cap which is engageable with said first end of said housing;
    (e) providing a front cap which is slidably engaged with said second end of said housing;
    (f) providing a spring-loaded needle holder within said front cap, said spring-loaded needle holder being engaged with a center of said second end of said housing;
    (g) forming a through hole at a distal end of said front cap;
    (h) mounting a needle in said spring-loaded needle holder, said needle being aligned with said through hole of front cap; and
    (i) providing a dust cover for said front cap.

2. The method of indicating a user's name on a blood-sampling needle pen as claimed in claim 1, wherein said housing is made of transparent materials.

3. The method of indicating a user's name on a blood-sampling needle pen as claimed in claim 1, wherein said housing has a plurality of locking flakes sildably engageable with grooves of said front cap.

* * * * *